United States Patent
Zhou

(12) 
(10) Patent No.: US 6,575,920 B2
(45) Date of Patent: Jun. 10, 2003

(54) DISTAL TIP PORTION FOR A GUIDE WIRE

(75) Inventor: Pu Zhou, Eden Prairie, MN (US)

(73) Assignee: SciMed Life Systems, Inc., Maple Grove, MN (US)

(*) Notice: Subject to any disclaimer, the term of this patent is extended or adjusted under 35 U.S.C. 154(b) by 8 days.

(21) Appl. No.: 09/870,324

(22) Filed: May 30, 2001

(65) Prior Publication Data

US 2002/0183654 A1 Dec. 5, 2002

(51) Int. Cl.[7] .............. A61B 5/00; A61B 6/00; A61M 25/00; A61M 5/178; A61M 5/00

(52) U.S. Cl. ............... 600/585; 600/433; 600/434; 600/435; 604/164.13; 604/264

(58) Field of Search .................. 600/433, 435, 600/585; 604/524, 264, 164.13, 528

(56) References Cited

U.S. PATENT DOCUMENTS

| | | | | |
|---|---|---|---|---|
| 4,456,017 A | * | 6/1984 | Miles ................... 128/772 |
| 4,719,924 A | * | 1/1988 | Crittenden et al. ........ 128/772 |
| 4,813,434 A | * | 3/1989 | Buchbinder et al. ....... 128/772 |
| 4,815,478 A | | 3/1989 | Buchbinder et al. ....... 128/772 |
| 4,886,067 A | * | 12/1989 | Palermo ................. 128/657 |
| 4,921,482 A | * | 5/1990 | Hammerslag et al. ...... 604/95 |
| 4,984,581 A | | 1/1991 | Stice ................... 128/772 |
| 5,045,061 A | | 9/1991 | Seifert et al. ............ 604/96 |
| 5,069,217 A | | 12/1991 | Fleischhacker, Jr. ....... 128/657 |
| 5,095,915 A | | 3/1992 | Engelson ............... 128/772 |
| 5,211,636 A | | 5/1993 | Mische ................. 604/264 |
| 5,217,026 A | | 6/1993 | Stoy et al. ............. 128/772 |
| 5,318,041 A | | 6/1994 | DuBois et al. ........... 607/119 |
| 5,333,620 A | | 8/1994 | Moutafis et al. ......... 128/772 |
| 5,345,945 A | | 9/1994 | Hodgson et al. ......... 128/772 |
| 5,368,048 A | | 11/1994 | Stoy et al. ............. 128/772 |
| 5,372,144 A | | 12/1994 | Mortier et al. .......... 128/772 |
| 5,376,083 A | | 12/1994 | Mische ................. 604/264 |
| 5,377,690 A | | 1/1995 | Berthiaume ............. 128/772 |
| 5,409,015 A | | 4/1995 | Palermo ................ 128/772 |
| 5,460,187 A | | 10/1995 | Daigle et al. ........... 123/772 |
| 5,480,382 A | | 1/1996 | Hammerslag et al. ...... 604/95 |
| 5,599,492 A | | 2/1997 | Engelson .............. 264/167 |
| 5,606,981 A | | 3/1997 | Tartacower et al. ....... 128/772 |
| 5,636,642 A | | 6/1997 | Palermo ................ 128/772 |
| 5,682,894 A | * | 11/1997 | Orr et al. .............. 128/654 |
| 5,762,615 A | | 6/1998 | Weier .................. 600/585 |
| 5,769,796 A | | 6/1998 | Palermo et al. ......... 600/585 |
| 5,772,609 A | * | 6/1998 | Nguyen et al. .......... 600/585 |
| 5,813,997 A | | 9/1998 | Imran et al. ........... 600/585 |
| 5,827,201 A | | 10/1998 | Samson et al. ......... 600/585 |
| 5,827,225 A | | 10/1998 | Ma Schwab ............ 604/96 |
| 5,833,631 A | | 11/1998 | Nguyen ............... 600/585 |
| 5,836,893 A | | 11/1998 | Urick ................. 600/585 |
| 5,916,178 A | * | 6/1999 | Noone et al. .......... 600/585 |
| 5,984,878 A | | 11/1999 | Engelson ............. 600/585 |
| 6,106,488 A | | 8/2000 | Fleming et al. ........ 600/585 |
| 6,132,388 A | | 10/2000 | Fleming et al. ........ 600/585 |
| 6,139,510 A | | 10/2000 | Palermo .............. 600/585 |
| 6,139,511 A | | 10/2000 | Huter et al. .......... 600/585 |
| 6,165,140 A | | 12/2000 | Ferrera .............. 600/585 |
| 6,352,515 B1 | * | 3/2002 | Anderson et al. ....... 600/585 |
| 2001/0009981 A1 | * | 7/2001 | DuBois et al. ......... 600/585 |

FOREIGN PATENT DOCUMENTS

| | | |
|---|---|---|
| EP | 0 739 641 | 10/1996 |
| GB | 1 304 231 | 1/1973 |
| WO | WO 98/58697 | 12/1998 |

* cited by examiner

Primary Examiner—Timothy L. Maust
Assistant Examiner—Anuradha Ramana
(74) Attorney, Agent, or Firm—Crompton, Seager & Tufte, LLC

(57) ABSTRACT

Methods and devices relating to guidewires. In one embodiment, a distal tip portion of a guidewire comprises a first tip member and a second tip member. The first tip member has a first end, and a second end. The second tip member has a distal portion and a proximal portion. The first and second tip members are coupled together, preferably in an arrangement that can effect the flexibility of the guidewire at certain points along its length.

28 Claims, 4 Drawing Sheets

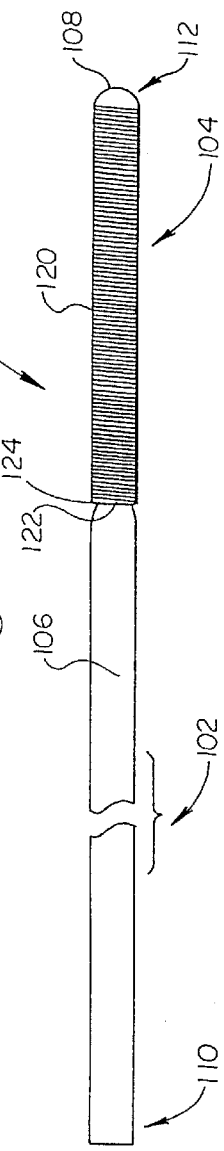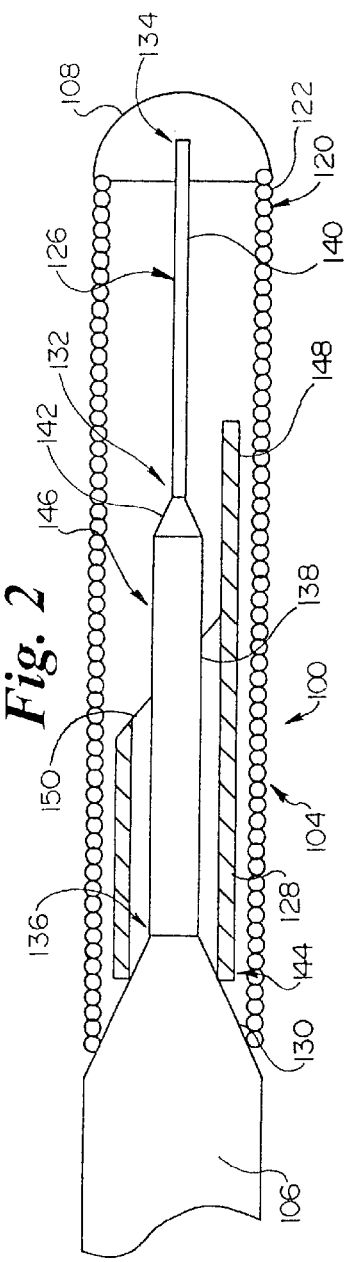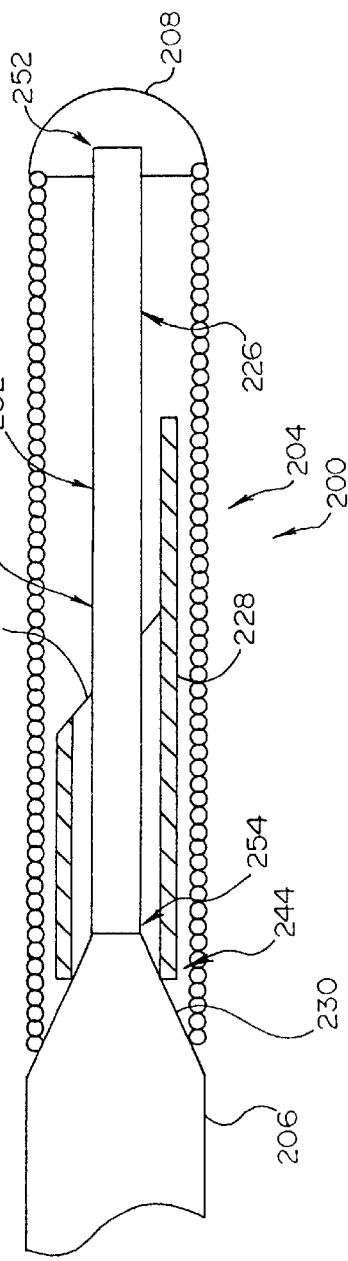

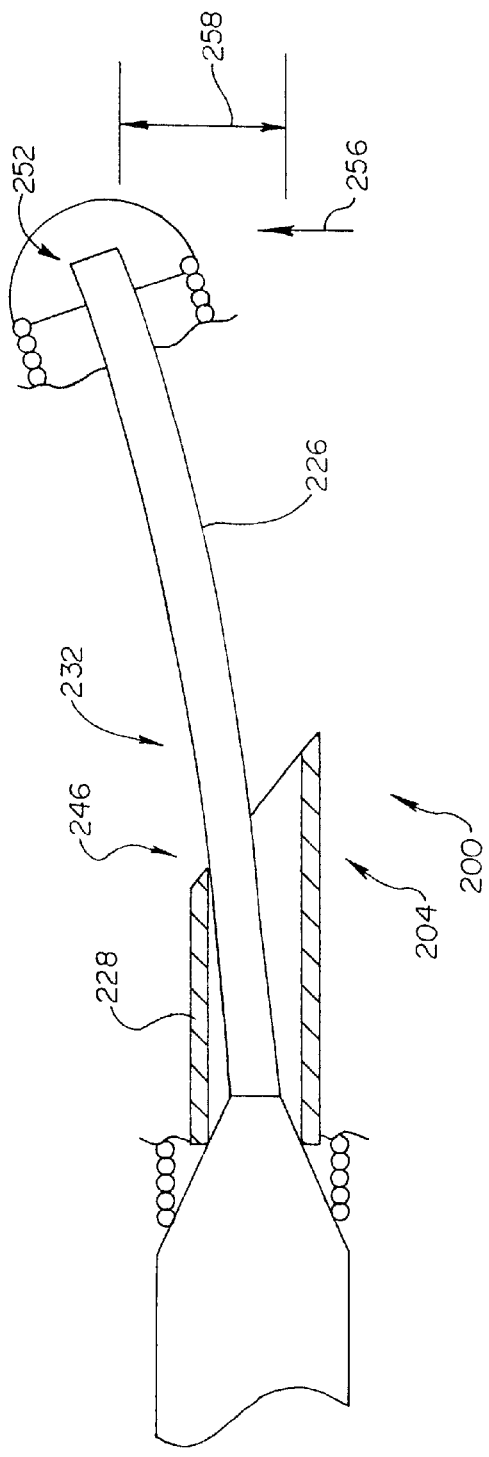
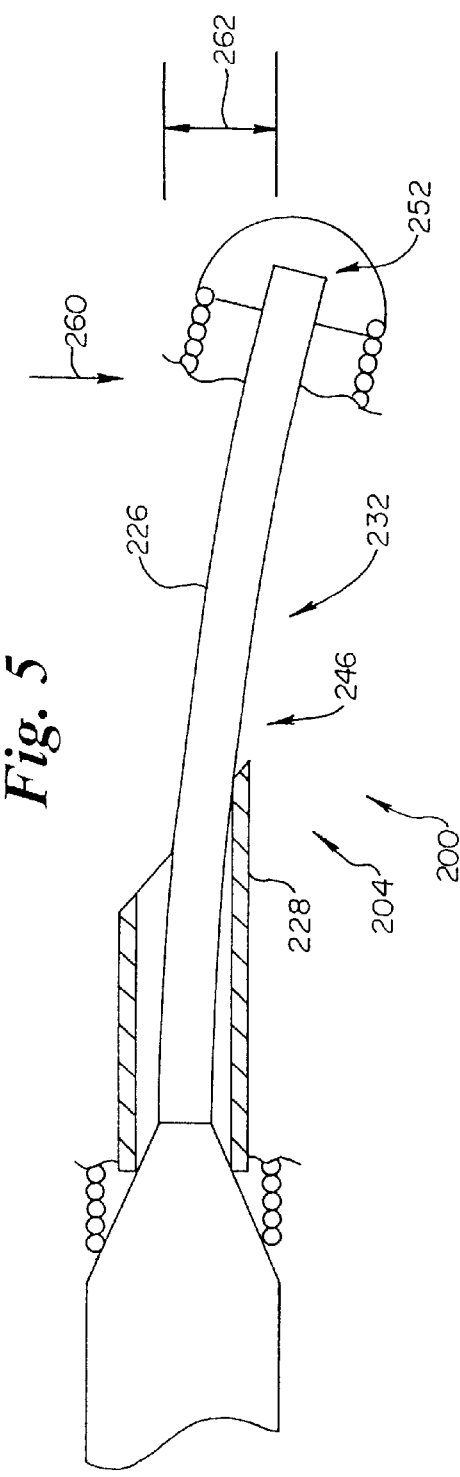

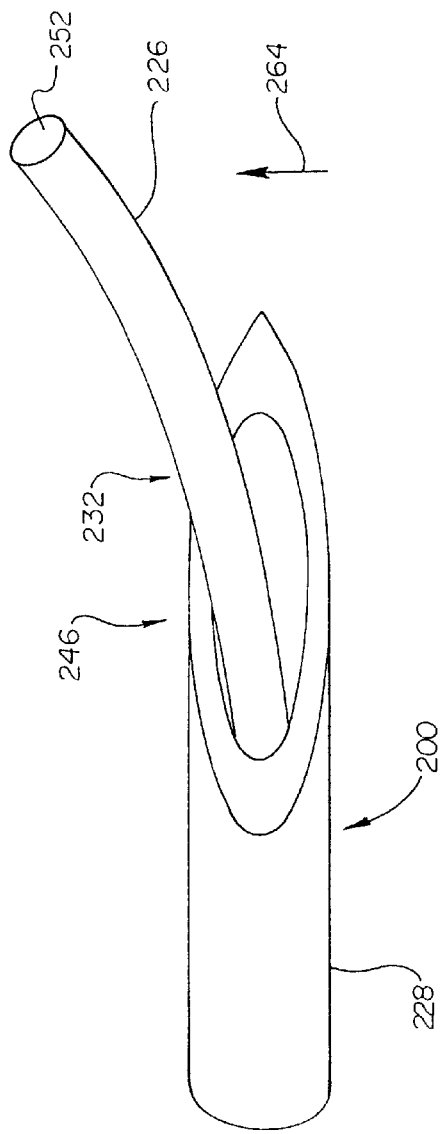
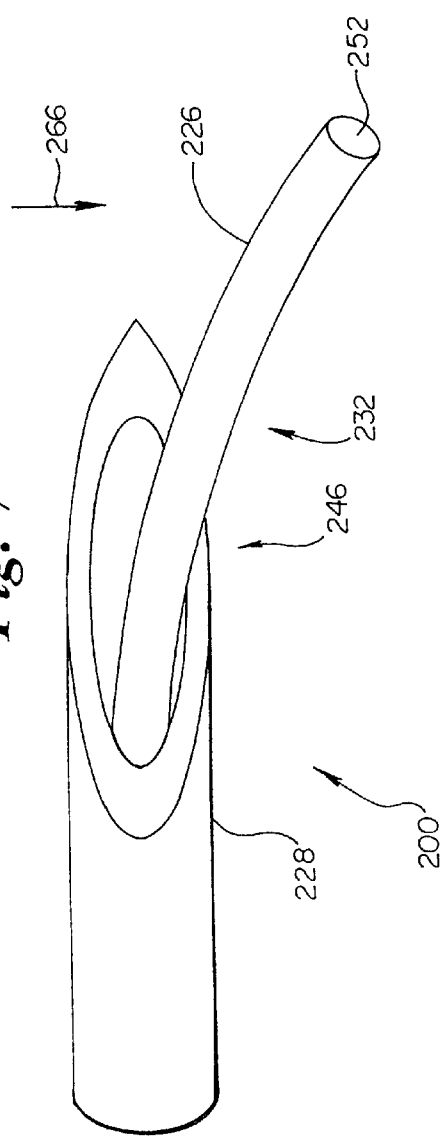

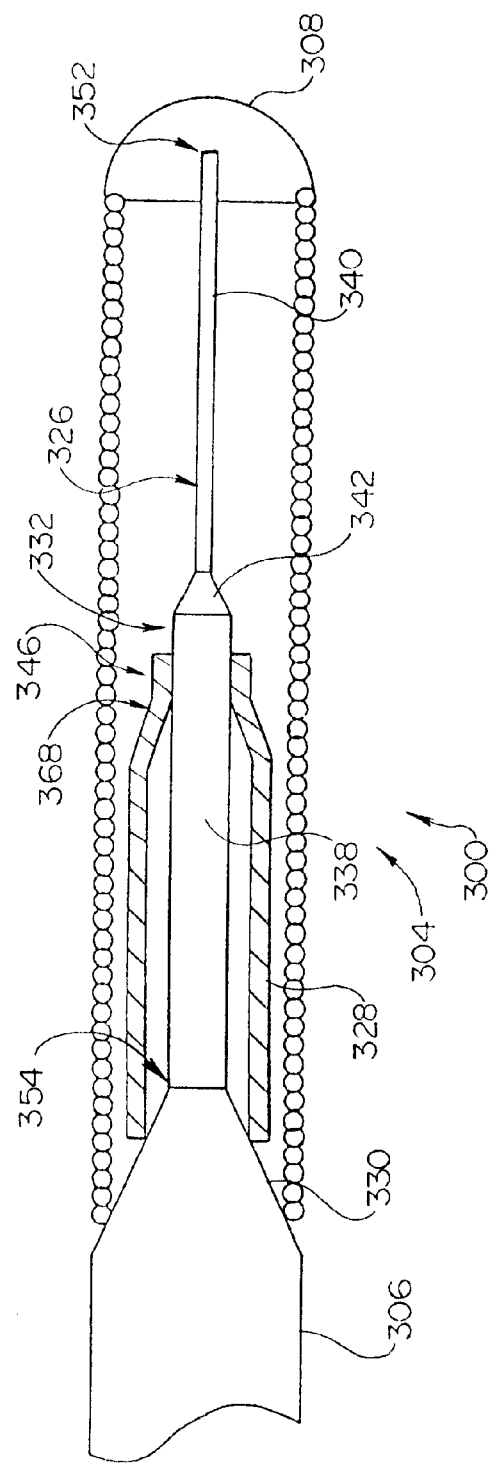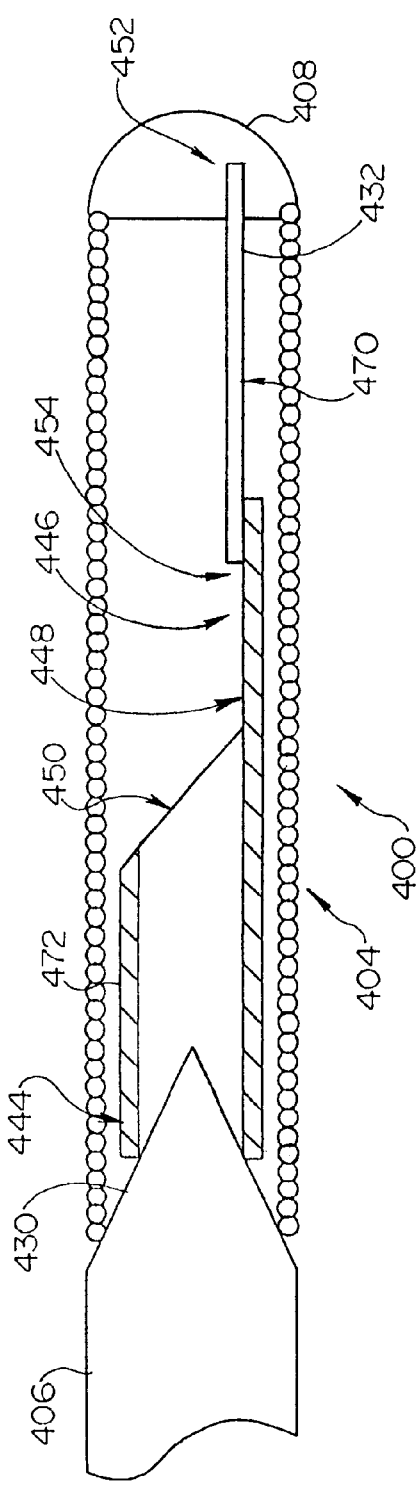

DISTAL TIP PORTION FOR A GUIDE WIRE

FIELD OF THE INVENTION

The invention is directed to guidewires. More particularly, the invention relates to guidewires having a relatively longitudinally stiff proximal portion, and a relatively laterally flexible distal portion.

BACKGROUND OF THE INVENTION

It is often desirable to combine a number of performance features in a guidewire. For example, it is often desirable that a guidewire be relatively laterally flexible at certain points along its length, for example, near its distal end.

SUMMARY OF THE INVENTION

The invention is directed to guidewires. One embodiment includes a guidewire including a first tip member and a second tip member. The first tip member has a first end, and a second end. The second tip member has a distal portion and a proximal portion. The two tip members are coupled together, preferably in an arrangement that can effect the flexibility of the guidewire at certain points along its length.

BRIEF DESCRIPTION OF THE DRAWINGS

FIG. 1 is a plan view of a guidewire in accordance with an exemplary embodiment of the invention;

FIG. 2 is a partial cross-sectional view of a distal tip portion of the guidewire of FIG. 1;

FIG. 3 is a partial cross-sectional view of a distal tip portion of a guidewire in accordance with an additional exemplary embodiment of the invention;

FIG. 4 is an additional partial cross-sectional view of a distal tip portion of the guidewire of FIG. 3;

FIG. 5 is an additional partial cross-sectional view of a distal tip portion of the guidewire of FIG. 3;

FIG. 6 is a perspective view of a distal tip portion of the guidewire of FIG. 3;

FIG. 7 is an additional perspective view of a distal tip portion of the guidewire of FIG. 3;

FIG. 8 is a partial cross-sectional view of a distal tip portion of a guidewire in accordance with an additional exemplary embodiment of the invention; and FIG. 9 is a partial cross-sectional view of a distal tip portion of a guidewire in accordance with an additional exemplary embodiment of the invention.

DETAILED DESCRIPTION OF THE INVENTION

The following detailed description should be read with reference to the drawings, in which like elements in different drawings are numbered in like fashion. The drawings, which are not necessarily to scale, depict selected embodiments and are not intended to limit the scope of the invention. In some cases, the drawings may be highly diagrammatic in nature. Examples of constructions, materials, dimensions, and manufacturing processes are provided for various elements. Those skilled in the art will recognize that many of the examples provided have suitable alternatives which may be utilized.

FIG. 1 is a plan view of a guidewire 100 in accordance with the invention. Guidewire 100 includes an elongate proximal portion 102 terminating at a proximal end 110 and distal tip portion 104 terminating at a distal end 112. Elongate proximal portion 102 comprises an elongate body member 106. Distal tip portion 104 includes an atraumatic tip 108 and a sheath 120. In a preferred embodiment, the distal end of sheath 120 is fixed to atraumatic tip 108 and the proximal end of sheath 120 is fixed to elongate body member 106.

The sheath 120 comprises a wire 122 forming a plurality of turns 124. In a preferred embodiment, adjacent turns 124 are disposed in close proximity to one another. In a particularly preferred embodiment, adjacent turns 124 contact each other across substantially their entire length. In this particularly preferred embodiment, sheath 120 has a high level of longitudinal pushability and a high level of lateral flexibility.

FIG. 2 is a partial cross-sectional view of distal tip portion 104 of guidewire 100 of FIG. 1. In FIG. 2, it may be appreciated that atraumatic tip 108 of guidewire 100 is fixed to a distal end 134 of a first tip member 126 that extends distally from a body taper 130 of elongate body member 106. An intermediate portion 132 of first tip member 126 extends between distal end 134 of first tip member 126 and a proximal end 136 of first tip member 126. Intermediate portion 132 of first tip member 126 comprises a proximal segment 138, a distal segment 140, and a tapered portion 142 extending between proximal segment 138 and distal segment 140.

Distal tip portion 104 of guidewire 100 also includes a second tip member 128. In a preferred embodiment, a proximal portion 144 of second tip member 128 is coupled to end 136 of first tip member 126. Proximal portion 144 of second tip member 128 is fixed to body taper 130 of elongate body member 106 such that second tip member 128 is coupled to first tip member 126 via body taper 130. Second tip member 128 may be fixed to body taper 130 of elongate body member 106 in various ways. Some examples of suitable methods of fixing second tip member 128 to elongate body member 106 include soldering, brazing, adhesive bonding, welding and the like. It is to be appreciated that various welding processes may be utilized without deviating from the spirit and scope of the present invention. Examples of welding processes that may be suitable in some applications include LASER welding, resistance welding, TIG welding, and microplasma welding. LASER welding equipment that may be suitable in some applications is commercially available from Unitek Miyachi of Monrovia, Calif. and Rofin-Sinar Incorporated of Plymouth, Mich. Resistance welding equipment that may be suitable in some applications is commercially available from Palomar Products Incorporated of Carlsbad, Calif. and Polaris Electronics of Olathe, Kans. TIG welding equipment that may be suitable in some applications is commercially available from Weldlogic Incorporated of Newbury Park, Calif. Microplasma welding equipment that may be suitable in some applications is commercially available from Process Welding Systems Incorporated of Smyrna, Tenn.

The distal portion of slope 150 and/or tong 148 can be attached to the first tip member 126 using adhesives, for example polyurethane, silicone, cyanoacrylates, epoxies, and the like.

A distal portion 146 of second tip member 128 is disposed about intermediate portion 132 of first tip member 126. Preferably, distal portion 146 of second tip member 128 includes a slope 150 and a tong 148 that extends distally from second tip member 128. It should be noted that embodiments of second tip member 128 are possible in which distal portion 146 does not include tong 148. In a preferred embodiment, second tip member 128 comprises a tubular wall defining a lumen.

Preferably, the shape of the distal portion 146 is arranged and configured such that the distance that the first tip member 126 deflects in a first direction before engaging the distal portion 146 of the second tip member 228 is different than the distance that the first tip member 126 deflects in a second direction before intermediate portion 132 of the first tip member 126 engages second tip member 128. Preferably, the lateral stiffness of the distal portion 146 of the guidewire 100 changes when the first tip member 126 engages the second tip member 128.

In a preferred embodiment, second tip member 128 comprises a shape memory material. Examples of shape memory materials which may be suitable in some applications include shape memory polymers and shape memory alloys. Examples of shape memory alloys which may be suitable in some applications include nitinol. The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL). Nitinol is commercially available from Memry Technologies (Brookfield, Conn.), TiNi Alloy Company (San Leandro, Calif.), and Shape Memory Applications (Sunnyvale, Calif.). In an especially preferred embodiment, second tip member 128 comprises superelastic nitinol.

In FIG. 2, it may be appreciated that wire 122 of sheath 120 of distal tip portion 104 has a generally circular cross-sectional shape. The term "wire", as used in describing wire 122, should not be mistaken as limiting wire 122 to elements having a circular cross section. The cross section of wire 122 may be any number of shapes. For example, the cross section of wire 122 could be rectangular, elliptical, and the like. Likewise, the term "wire", as used in describing wire 122, should not be mistaken as being limited to metallic materials. In fact, wire 122 may be comprised of many metallic and non-metallic materials. Examples of metallic materials that may be suitable in some applications include stainless steel, nitinol, tantalum, gold, and titanium. Examples of non-metallic materials that may be suitable in some applications may be found in the list immediately below which is not exhaustive: polycarbonate, poly(L-lactide) (PLLA), poly(D,L-lactide) (PLA), polyglycolide (PGA), poly(L-lactide-co-D,L-lactide) (PLLA/PLA), poly (L-lactide-co-glycolide) (PLLA/PGA), poly(D, L-lactide-co-glycolide) (PLA/PGA), poly(glycolide-co-trimethylene carbonate) (PGA/PTMC), polyethylene oxide (PEO), polydioxanone (PDS), polycaprolactone (PCL), polyhydroxylbutyrate (PHBT), poly(phosphazene), polyD,L-lactide-co-caprolactone) (PLA/PCL), poly(glycolide-co-caprolactone) (PGA/PCL), polyanhydrides (PAN), poly(ortho esters), poly (phoshate ester), poly(amino acid), poly(hydroxy butyrate), polyacrylate, polyacrylamid, poly(hydroxyethyl methacrylate), polyurethane, polysiloxane and their copolymers. Embodiments of the present invention have also been envisioned in which wire 122 has a tubular cross section.

FIG. 3 is a partial cross-sectional view of a distal tip portion 204 of a guidewire 200 in accordance with an additional exemplary embodiment of the invention. In FIG. 3, it may be appreciated that distal tip portion 204 of guidewire 200 includes a first tip member 226 having a first end 252, a second end 254, and an intermediate portion 232 extending therebetween. First end 252 of first tip member 226 is fixed to an atraumatic tip 208 of guidewire 200. Second end 254 of first tip member is fixed to an elongate body member 206 of guidewire 200.

Distal tip portion 204 of guidewire 200 also includes a second tip member 228. In a preferred embodiment, a proximal portion 244 of second tip member 228 is coupled to the second end 254 of first tip member 226. Proximal portion 244 of second tip member 228 is fixed to body taper 230 of elongate body member 206 such that second tip member 228 is coupled to first tip member 226 via body taper 230. Second tip member 228 may be fixed to body taper 230 of elongate body member 206 in various ways. Methods of fixing second tip member 228 to elongate body member 206 that may be suitable in some applications include soldering, brazing, adhesive bonding, welding, and the like.

A distal portion 246 of second tip member 228 is disposed about intermediate portion 232 of first tip member 226. In a preferred embodiment, first tip member 226 and second tip member 228 are configured such that intermediate portion 232 of first tip member 226 engages distal portion 246 of second tip member 228 after a pre-selected deflection of first tip member 226. For example, intermediate portion 232 of first tip member 226 may seat against and/or couple with distal portion 246 of second tip member 228. In a preferred embodiment, the lateral stiffness of distal tip portion 204 of guidewire 200 changes when intermediate portion 232 of first tip member 226 engages distal portion 246 of second tip member 228.

It is to be appreciated that embodiments of distal tip portion 204 are possible in which an adhesive joint is disposed between intermediate portion 232 of first tip member 226 and distal portion 246 of second tip member 228. Embodiments of distal tip portion 204 are possible in which a soft polymer tube is disposed between first tip member 226 and second tip member 228.

Distal portion 246 of second tip member 228 includes a slope 250. In a preferred embodiment, the shape of distal portion 246 may preferably be selected so that the distance that first tip member 226 deflects in a first direction before engaging second tip member 228 is different than the distance that first tip member 226 deflects in a second direction before intermediate portion 232 of first tip member 226 engages second tip member 228.

FIG. 4 is an additional partial cross-sectional view of distal tip portion 204 of guidewire 200 of FIG. 3. First tip member 226 has been deflected in a first direction 256 such that first end 252 has been displaced by a first distance 258. In FIG. 4, it may be appreciated that intermediate portion 232 of first tip member 226 is seated against distal portion 246 of second tip member 228. In a preferred embodiment, first tip member 226 and second tip member 228 are configured such that intermediate portion 232 of first tip member 226 engages distal portion of second tip member 228 after a pre-selected deflection in first direction 256. Also in a preferred embodiment, the lateral stiffness of distal tip portion 204 of guidewire 200 changes when intermediate portion 232 of first tip member 226 engages distal portion 246 of second tip member 228.

FIG. 5 is an additional partial cross-sectional view of distal tip portion 204 of guidewire 200 of FIG. 3. First tip member 226 has been deflected in a second direction 260 such that first end 252 has been displaced by a second distance 262. In FIG. 5, it may be appreciated that intermediate portion 232 of first tip member 226 is seated against distal portion 246 of second tip member 228. In a preferred embodiment, first tip member 226 and second tip member 228 are configured such that intermediate portion 232 of first tip member 226 engages distal portion 246 of second tip member 228 after a pre-selected deflection in second direction 260. Also in a preferred embodiment, the lateral stiffness of distal tip portion 204 of guidewire 200 changes when intermediate portion 232 of first tip member 226 engages distal portion 246 of second tip member 228.

FIG. 6 is a perspective view of first tip member 226 and second tip member 228 of guidewire 200 of FIG. 3. For purposes of simplicity and clarity, only first tip member 226 and second tip member 228 are shown in FIG. 6. In the embodiment of FIG. 6, first tip member 226 has been deflected in a third direction 264 such that first end 252 has been displaced by a third distance. In FIG. 6, it may be appreciated that intermediate portion 232 of first tip member 226 is seated against distal portion 246 of second tip member 228. In a preferred embodiment, first tip member 226 and second tip member 228 are configured such that intermediate portion 232 of first tip member 226 engages distal portion of second tip member 228 after a pre-selected deflection in third direction 264. Also in a preferred embodiment, the lateral stiffness of distal tip portion 204 of guidewire 200 changes when intermediate portion 232 of first tip member 226 engages distal portion 246 of second tip member 228.

FIG. 7 is a perspective view of first tip member 226 and second tip member 228 of guidewire 200 of FIG. 3. For purposes of simplicity and clarity, only first tip member 226 and second tip member 228 are shown in FIG. 7. First tip member 226 has been deflected in a fourth direction 266 such that first end 252 has been displaced by a fourth distance. In FIG. 7, it may be appreciated that intermediate portion 232 of first tip member 226 is seated against distal portion 246 of second tip member 228. In a preferred embodiment, first tip member 226 and second tip member 228 are configured such that intermediate portion 232 of first tip member 226 engages distal portion 246 of second tip member 228 after a pre-selected deflection in fourth direction 266. Also in a preferred embodiment, the lateral stiffness of distal tip portion 204 of guidewire 200 changes when intermediate portion 232 of first tip member 226 engages distal portion 246 of second tip member 228. In the embodiment of FIG. 6 and FIG. 7, the third distance is preferably substantially equal to the fourth distance.

FIG. 8 is a partial cross-sectional view of a distal tip portion 304 of a guidewire 300 in accordance with an additional exemplary embodiment of the invention. In FIG. 8, it may be appreciated that distal tip portion 304 of guidewire 300 includes a first tip member 326 having a first end 352, a second end 354, and an intermediate portion 332 extending therebetween. First end 352 of first tip member 326 is fixed to an atraumatic tip 308 of guidewire 300. Second end 354 of first tip member is fixed to an elongate body member 306 of guidewire 300. Intermediate portion 332 of first tip member 326 comprises a proximal segment 338, a distal segment 340, and a tapered portion 342 extending between proximal segment 338 and distal segment 340.

Distal tip portion 304 of guidewire 300 also includes a second tip member 328 which is disposed about first tip member 326. In a preferred embodiment, a proximal portion 344 of second tip member 328 is coupled to second end 354 of first tip member 326. A proximal portion 344 of second tip member 328 is fixed to a body taper 330 of elongate body member 306 such that second tip member 328 is coupled to first tip member 326 via body taper 330. Second tip member 328 may be fixed to body taper 330 of elongate body member 306 in various ways. Methods of fixing second tip member 328 to elongate body member 306 that may be suitable in some applications include soldering, brazing, adhesive bonding, welding, and the like.

A distal portion 346 of second tip member 328 is disposed about intermediate portion 332 of first tip member 326. Second tip member 328 comprises a tubular wall defining a lumen. Distal portion 346 includes a necked portion 368. In a particularly preferred embodiment, second tip member 328 comprises nitinol. In an especially preferred embodiment, second tip member 328 comprises superelastic nitinol. When second tip member 328 comprises nitinol, necked portion 368 of second tip member 328 preferably provides a smooth transition in the lateral stiffness of distal tip portion 304 of guidewire 300.

FIG. 9 is a partial cross-sectional view of a distal tip portion 404 of a guidewire 400 in accordance with yet another exemplary embodiment of the invention. In FIG. 9, it may be appreciated that distal tip portion 404 of guidewire 400 includes a distal tip member 470 having a first end 452, a second end 454, and an intermediate portion 432 extending therebetween. First end 452 of distal tip member 470 is fixed to an atraumatic tip 408 of guidewire 400.

Second end 454 of distal tip member 470 is fixed to a distal portion 446 of a second tip member 472. A proximal portion 444 of second tip member 472 is fixed to a body taper 430 of an elongate body member 406 of guidewire 400. Methods of fixing second tip member 472 to elongate body member 406 that may be suitable in some applications include soldering, brazing, adhesive bonding, welding, and the like.

In a preferred embodiment, second tip member 472 comprises a tubular wall defining a lumen. A distal portion 446 of second tip member 472 includes a slope 450 and a tong 448 that extends distally from intermediate tip member 472. In a particularly preferred embodiment, second tip member 472 comprises nickel and titanium. In an especially preferred embodiment, second tip member 472 comprises nitinol.

Guidewires embodying the invention can be utilized in a wide variety of medical procedures. For example, guidewires are often utilized to assist in advancing the intravascular catheter through the vasculature of a patient. A guidewire may be inserted into the vascular system of the patient at an easily accessible location and urged forward through the vasculature until the tip of the guidewire is proximate the target site. A proximal end of the guidewire may then be inserted into a guidewire lumen of a catheter. The tip of the catheter may be advanced along the length of the guidewire until it reaches the target site.

Typically, the guidewire enters the patient's vasculature at a convenient location such as a blood vessel in the neck or near the groin. Once the distal portion of the guidewire has entered the patient's vascular system, the physician may urge the distal tip forward by applying longitudinal forces to the proximal portion of the guidewire. For the guidewire to effectively communicate these longitudinal forces, it is desirable that the guidewire have a high level of pushability and kink resistance, particularly near its proximal end.

The path taken by a guidewire through the vascular system is often tortuous, requiring the guidewire to change direction frequently. In some cases, it may even be necessary for the guidewire to double back on itself. In order for the guidewire to conform to a patient's tortuous vascular system, it is desirable that guidewires be laterally flexible, particularly near the distal end.

While advancing the guidewire through the tortuous path of the patient's vasculature, physicians often apply torsional forces to the proximal portion of the guidewire to aid in steering the guidewire. To facilitate the steering process, the distal portion of the guidewire may be bent by the physician. Torsional forces applied on the proximal end must translate to the distal end to aid in steering. It is therefore desirable that the proximal portion of a guidewire have a relatively high level of torqueability to facilitate steering.

The distance between the access site and the target site is often in excess of 100 cm. The inside diameter of the vasculature at the access site is often less than 5 mm. In light of the geometry of the patient's body, it is desirable to combine the features of torqueability, pushability, and flexibility into a guidewire that is relatively long and has a relatively small diameter.

Ideally, the distal end of a guidewire will be adapted to reduce the probability that the vascular tissue will be damaged as the guidewire progresses through the vascular system. This is sometimes accomplished by fixing a rounded tip member to the distal end of the guidewire.

After the guidewire has been navigated through the patient's vascular system so that its distal end is adjacent the target site, an intravascular catheter may be advanced over the guidewire. The catheter may be used for various diagnostic and/or therapeutic purposes. One example of a diagnostic use for a catheter is the delivery of radiopaque contrast solution to enhance fluoroscopic visualization. In this application, the catheter provides a fluid path leading from a location outside the body to a desired location inside the body of a patient.

Examples of therapeutic purposes for catheters include percutaneous transluminal angioplasty (PTA) and percutaneous transluminal coronary angioplasty (PTCA). These angioplasty techniques typically involve the use of a balloon catheter. During these procedures, the distal end of the guidewire is often positioned in the ostium of the coronary artery. The balloon catheter may then be advanced over the guidewire such that the balloon is positioned proximate the restriction in the diseased vessel. The balloon is then inflated and the restriction in the vessel is opened. In this application, it is desirable that the guidewire provide a low friction path for the balloon catheter.

One additional example of a useful therapeutic application of catheters is the treatment of intracranial aneurysms in the brain. An aneurysm which is likely to rupture, or one which has already ruptured may be treated by delivering an embolic device to the interior of the aneurysm. The embolic device encourages the formation of a thrombus inside the aneurysm. The formation of a thrombus reduces the probability that an aneurysm will rupture. Or, in cases where an aneurysm has already ruptured, the formation of a thrombus will reduce the probability that the previously ruptured aneurysm will re-bleed. One commonly used embolic device comprises a tiny coil of wire.

When treating an aneurysm with the aid of a catheter, the catheter tip is typically positioned proximate the aneurysm site. The embolic device is then urged through the lumen of the catheter and introduced into the aneurysm. Shortly after the thrombus agent is placed in the aneurysm, a thrombus forms in the aneurysm and is shortly thereafter complemented with a collagenous material that significantly lessens the potential for aneurysm rupture.

Having thus described some embodiments of the present invention, those of skill in the art will readily appreciate that yet other embodiments may be made and used within the scope of the claims hereto attached. Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is defined in the language in which the appended claims are expressed.

What is claimed is:

1. A guidewire comprising;
    a first tip member having a first end, and a second end;
    a second tip member including a proximal portion and a distal portion;
    the proximal portion of the second tip member being coupled to the second end of the first tip member; and
    wherein the first tip member and the second tip member are configured such that a portion of the first tip member does not engage the distal portion of the second tip member prior to the application of a pre-selected lateral deflection of the first tip member, and the portion of the first tip member engages the distal portion of the second tip member after the application of the pre-selected lateral deflection of the first tip member such that a lateral stiffness of a portion of the guidewire changes when the first tip member engages the second tip member.

2. The guidewire of claim 1, wherein the second tip member comprises a shape memory material.

3. The guidewire of claim 2, wherein the shape memory material comprises a shape memory alloy.

4. The guidewire of claim 3, wherein the shape memory alloy comprises nitinol.

5. The guidewire of claim 1, further including an adhesive disposed between the first tip member and the second tip member.

6. The guidewire of claim 1, wherein the second tip member is generally disposed about the first tip member.

7. The guidewire of claim 1, wherein the second tip member comprises a tubular wall defining a lumen and the first tip member is disposed within the lumen.

8. The guidewire of claim 1, wherein the second tip member includes a tapered portion and a tong portion.

9. The guidewire of claim 1, further including an elongate body member having a body taper; and
    wherein a proximal portion of the second tip member is fixed to the body taper of the elongate body member.

10. The guidewire of claim 1, wherein the first tip member comprises:
    a proximal segment;
    a distal segment; and
    a tapered portion extending between the proximal segment and the distal segment.

11. A guidewire comprising;
    a first tip member having a first end, and a second end;
    a second tip member including a proximal portion and a distal portion;
    the proximal portion of the second tip member being coupled to the second end of the first tip member;
    wherein the first tip member and the second tip member are configured such that a portion of the first tip member engages the distal portion of the second tip member after a pre-selected first deflection of the first tip member in a first direction;
    wherein the first tip member and the second tip member are configured such that a portion of the first tip member engages the distal portion of the second tip member after a pre-selected second deflection of the first tip member in a second direction; and wherein a magnitude of the first deflection is different from a magnitude of the second deflection.

12. The guidewire of claim 11, wherein the guidewire is configured such that a lateral stiffness of a portion of the guidewire changes when the first tip member engages the second tip member.

13. The guidewire of claim 11, wherein the second tip member comprises a shape memory material.

14. The guidewire of claim 13, wherein the shape memory material comprises a shape memory alloy.

15. The guidewire of claim 14, wherein the shape memory alloy comprises nitinol.

16. The guidewire of claim 11, further including an adhesive disposed between the first tip member and the second tip member.

17. The guidewire of claim 11, wherein the second tip member is generally disposed about the first tip member.

18. The guidewire of claim 11, wherein the second tip member comprises a tubular wall defining a lumen and the first tip member is disposed within the lumen.

19. The guidewire of claim 11, wherein the second tip member includes a tapered portion and a tong portion.

20. The guidewire of claim 11, further including an elongate body member having a body taper; and wherein a proximal portion of the second tip member is fixed to the body taper of the elongate body member.

21. The guidewire of claim 11, wherein the first tip member comprises:

a proximal segment;

a distal segment; and a tapered portion extending between the proximal segment and the distal segment.

22. A guidewire comprising;

a first tip member having a first end, and a second end;

a second tip member including a proximal portion and a distal portion;

the proximal portion of the second tip member being coupled to the second end of the first tip member; and means for selectively engaging the distal portion of the second tip member with the first tip member such that after the application of a pre-selected lateral deflection of the first tip member, a lateral stiffness of a portion of the guidewire changes when the first tip member engages the second tip member.

23. The guidewire of claim 22, wherein the second tip member comprises a shape memory material.

24. The guidewire of claim 23, wherein the shape memory material comprises a shape memory alloy.

25. The guidewire of claim 24, wherein the shape memory alloy comprises nitinol.

26. The guidewire of claim 22, further including an adhesive disposed between the first tip member and the second tip member.

27. The guidewire of claim 22, wherein the second tip member is generally disposed about the first tip member.

28. The guidewire of claim 22, further including an elongate body member having a body taper; and wherein a proximal portion of the second tip member is fixed to the body taper of the elongate body member.

* * * * *